United States Patent [19]

Longley et al.

[11] 4,310,683
[45] Jan. 12, 1982

[54] SULFOSUCCINATE DIESTERS

[75] Inventors: Kermit D. Longley, Park Forest; Anastasios J. Karalis, Chicago, both of Ill.

[73] Assignee: Witco Chemical Corporation, New York, N.Y.

[21] Appl. No.: 48,924

[22] Filed: Jun. 15, 1979

Related U.S. Application Data

[63] Continuation of Ser. No. 842,198, Oct. 14, 1977, abandoned, which is a continuation of Ser. No. 575,324, May 7, 1975, abandoned.

[51] Int. Cl.$^3$ ............................................. C07C 143/12
[52] U.S. Cl. .................................. 560/151; 252/354; 252/542; 252/545; 544/110; 560/196
[58] Field of Search ................ 560/151; 252/545, 557, 252/354; 544/110

[56] References Cited

U.S. PATENT DOCUMENTS

| | | | |
|---|---|---|---|
| 2,028,091 | 1/1936 | Jaeger | 560/151 |
| 3,080,280 | 3/1963 | Lindner | 560/151 |
| 3,928,422 | 12/1975 | Sundby | 560/151 |
| 4,056,558 | 11/1977 | Sundby | 560/151 |

*Primary Examiner*—Vivian Garner
*Attorney, Agent, or Firm*—Albert L. Gazzola; Morton Friedman

[57] ABSTRACT

Sulfosuccinate diesters in which one carboxyl group of the sulfosuccinate is esterified with an ethoxylated or propoxylated non-tertiary monoamine, for instance, a $C_8$–$C_{18}$ fatty amine, ethoxylated with 3 or 4 moles of ethylene oxide, to form a hydroxyl-containing tertiary amine, and in which the other carboxyl group of the sulfosuccinate is esterified with an α-monoepoxide such as propylene oxide, or higher α-monoepoxides, and method of preparation of such sulfosuccinate diesters. The said sulfosuccinate diesters have utility as surfactants, such as detergents and emulsifiers.

7 Claims, No Drawings

SULFOSUCCINATE DIESTERS

This is a continuation of application Ser. No. 842,198, filed Oct. 14, 1977, which is a continuation of application Ser. No. 575,324, filed May 7, 1975, both now abandoned.

Our invention relates to the preparation of certain types of novel sulfosuccinate diesters at least most of which can be represented by the following formula:

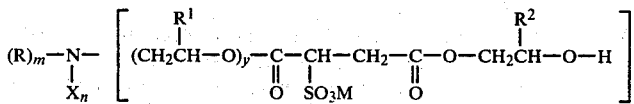

where R is alkyl; X is alkyl; $R^1$ is H or $CH_3$; $R^2$—O— is the radical of an α-epoxide (hereafter called α-epoxide) containing from 3 to 20 carbon atoms; M is an alkali metal, alkaline earth metal or organic substituted ammonium cation; m is 1 or 2; n is zero or 1; y is from 1 to 10 when $R^1$ is H and from 1 to 3 when $R^1$ is $CH_3$; w is 1 or 2; with the proviso that the sum of the number of carbon atoms in $(R)_m$ is from 2 to 24, and that there is a difference of at least 2 and, better still, at least 4 in the number of carbon atoms between the sum of the carbon atoms in (i) $(R)_m$—$N(X)_n$ and

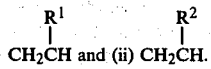

Most desirably, the difference in the number of carbon atoms between the sum of the number of carbon atoms in (i) $(R)_m$—$N(X)_n$ and

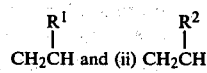

is between 4 and 14. Again, generally speaking, the preferred novel compounds of our present invention are those wherein, in the aforesaid formula, R is straight chain alkyl containing from 8 to 15 carbon atoms, m is 1, X is alkyl containing from 1 to 8 carbon atoms, $R^1$ is H, $R^2$ is $CH_3$, y is 2 to 6, and w is 1; and those wherein, in the aforesaid formula, R is straight chain alkyl containing from 3 to 5 carbon atoms, m is 1, X is alkyl containing from 8 to 15 carbon atoms, $R^1$ is H, $R^2$ contains from 6 to 14 carbon atoms, y is 2 to 6, and w is 1.

As will also be seen from the following description, certain of the sulfosuccinate diesters of the present invention may be described as those sulfosuccinate diesters in which one carboxyl group of the sulfosuccinate is esterified with a hydroxyl-containing tertiary amine in the form of an adduct of 2 mol of a $C_2$-$C_{24}$ aliphatic non-tertiary monoamine with from 1 to 10 moles of ethylene oxide or 1 to 3 mols of propylene oxide, and in which the other carboxyl group of the sulfosuccinate is reacted with a $C_3$-$C_{20}$ α-epoxide to form an ester group, subject to the proviso that there is a difference of at least 2, and, particularly, at least 4, carbon atoms between the number of carbon atoms in said adduct and the number of carbon atoms in said α-epoxide.

It is particularly desirable that the novel sulfosuccinate diester compounds of our present invention be marketed and used in the form of the aforementioned types of salts, that is, where M in formula (I) is an alkali metal (which term is here used to mean sodium, potassium, lithium and ammonium), or alkali earth metals, namely, calcium, magnesium, strontium and barium; or, as noted above, organic substituted ammonium or amines. These latter, which most advantageously are water-soluble lower molecular weight amines, may be selected from a wide group, typical examples of which are dimethylamine; diethylamine; triethylamine; propylamine; monoisopropylamine, diisopropylamine, triisopropylamine, and commercial mixtures of said isopropylamines; butyl amine, amyl amine; monoisopropanolamine, diisopropanolamine, triisopropanolamine and commercial mixtures of said isopropanolamines; ethanolamines such as monoethanolamine, diethanolamine, triethanolamine, and commercial mixtures thereof; polyamines such as aminoethyl ethanolamine, ethylenediamine, diethylenetriamine, hydroxyethyl ethylenediamine, and hexamethylenediamine; hexylamine; cyclohexylamine; dimethylbenzylamine, benzylamine; morpholine; etc. Such salts can be prepared from sodium or potassium salts of the novel sulfosuccinate diester compounds of our present invention by known metathesis techniques.

The aforesaid sulfosuccinate diester compounds are characterized by the fact that there is present in the molecules thereof, connected through an ester linkage to one of the carboxyl groups of maleic anhydride, a free hydroxyl group in the α-position resulting from the utilization of an α-epoxide containing at least 3 carbon atoms in the production of the compounds of our invention, and an ester linkage connected through the other one of the carboxyl groups of the maleic anhydride, all as is hereafter described in detail and illustrated by the various disclosed embodiments of our invention. The special combination of radicals in the compounds of our invention results in particular properties which effectively adapt various of the compounds to highly effective utilities in various environments.

In certain cases, the radical $(R)_m$—$N(X)_n$ in formula (I) will be derived from a long chain, for instance a $C_8$-$C_{20}$, aliphatic primary or secondary monoamine, and the radical

in said formula (I) will be derived from an α-epoxide such as propylene oxide or butylene oxide, particular propylene oxide. However, compounds according to and within the scope of our invention are also obtained where the $(R)_m$—$N(X)$—$_n$ radical of said formula (I) is derived from a $C_2$-$C_5$ aliphatic non-tertiary monoamine such as ethyl amine, n-propyl amine, isopropyl amine, n-butyl amine, isobutyl amine, n-pentyl amine and isopentyl amine, and the

radical is derived from a $C_3$–$C_{20}$, particularly a $C_8$–$C_{20}$, α-epoxide such as octylene oxide or dodecylene oxide or styrene oxide.

The aforesaid compounds are useful in various fields where surfactant or wetting-out properties are a desideratum such as, for instance, detergents, emulsifiers, penetrating agents, stabilizing agents, dispersants, emollients, and the like.

Certain sulfosuccinate esters are known to the art, being disclosed, for instance, in U.S. Pat. Nos. 2,028,091; 2,252,401; 2,316,234; 2,507,030; 2,887,504; 2,976,208; 2,976,209; 2,976,211; 3,002,994; 3,080,280; 3,123,640; 3,123,641; 3,141,905; 3,155,591; 3,404,164; 3,481,973; French Patent of Addition No. 69,516; and C. R. Caryl. Ind. Eng. Chem., 33, 731–7 (1941). However, so far as we are aware, there has been no prior suggestion of disclosure of any of the compounds of our invention.

In the preparation of various of the novel compounds of our invention, maleic anhydride is initially reacted with a hydroxyl-containing tertiary amine in the form of an adduct of 1 mol of an aliphatic non-tertiary monoamine with, for instance, 2 to 6 mols of ethylene oxide or 1 to 2 mols of propylene oxide, in proportions such as to produce predominately the maleic acid monoester, generally speaking, a mol ratio of 1 to about 1.2 mols of maleic anhydride to 1 mol of the adduct to produce a reaction product which contains upwards of 90 or 95% of the monoester. It is generally unnecessary to purify the reaction product to separate the monoester, but this can be done, if desired, by conventional purification techniques.

In one procedure for the production of the monoester of the adduct, the adduct and the maleic anhydride are initially admixed and reacted, for instance, at about 70° to about 100° C. until the acid number reaches or approximates that of the desired monoester. To said monoester is then added the selected α-epoxide in amounts to drive the desired reaction to completion which, in the usual cases, involves the employment of about 0.2 to 0.3 mols excess to effect completion of the reaction in a reasonable length of time. To the resulting diester there is then added slightly more than 1 mol of a bisulfite per mole of maleic anhydride used and the resulting mixture is heated until the reaction is complete. It should be noted that, in the preparation of the novel compounds of our present invention, whether by the preferred procedure described in this paragraph or otherwise in accordance with our invention, it is essential that maleic anhydride be utilized.

The preparation of adducts, namely, those of the non-tertiary aliphatic monoamines with ethylene oxide or propylene oxide is, per se, well known to the art. Also, the preparation of esters by the reaction of such adducts with maleic anhydride is, per se, known to the art. Various esterification procedures can be used and it is convenient, for example, to employ techniques such as are disclosed by Mehta et al, J. Org. Chem. 25,1012 (1960), utilizing an organic solvent reaction medium, such as anhydrous diethylether.

In the preparation of those of the compounds of our invention which are in the form of amine salts, it is sometimes desirable to produce such in substantially anhydrous form, soluble in organic solvents, particularly polar organic solvents such as ethyl alcohol, propyl alcohol, isopropyl alcohol, methyl and ethyl formamides, tc. To this end, for instance, the aforedescribed intermediate diesters can be reacted with a solution containing an organic amine, sufficient water to provide a reaction medium and containing dissolved sulfur dioxide to form a sulfite of said organic amine, and a water-miscible alcohol, for instance, methyl alcohol, ethyl alcohol, n-propanol or isopropyl alcohol, whereby to produce a substantially anhydrous organic amine salt of the said sulfosuccinic acid diesters. For best results, in carrying out such reaction, for each mol of said intermediate diester, the solution reacted therewith should contain about 1 mol or slightly more of organic amine or amines, and about 1 mol of water containing about 1 mol of sulfur dioxide.

In the preparation of the novel compounds of our invention by the foregoing method, it is important, in order to obtain said compounds, that the sequence of steps noted above be followed, that is, that the maleic acid monoester of the hydroxyl-containing tertiary amine in the form of the aforesaid adduct first be provided or prepared after which the raction with the α-epoxide is carried out, followed by the reaction with the aqueous bisulfite to introduce the sulfonic group into the molecule. Thus, for instance, if the α-epoxide is first reacted with the maleic anhydride and then with (a) the said adduct followed by the reaction with the aqueous bisulfite, or (b) the adduct bisulfite followed by the reaction with the said adduct, the products of or contemplated by the present invention are not obtained.

In the reaction of the monoesters with the α-epoxides containing at least 3 carbon atoms to produce the intermediate diesters which are then converted into the sulfosuccinate diesters of our invention, said reaction is especially desirably carried out in the presence of a catalyst, particularly a basic organic material such as, by way of example, tertiary amines such as triethylamine and triisopropylamine; tris dimethylamino methyl phenol; and quaternary ammonium salts such as tetramethyl ammonium hydroxide, tetraethyl ammonium hydroxide, benzyl trimethyl ammonium hydroxide and benzyl triethyl ammonium hydroxide. Inorganic basic catalysts such as sodium hydroxide or potassium hydroxide can be used but are not preferred. The catalysts can be used in variable proportions, generally in the range of 0.1 to 2 or 3%, based on the weight of the monoester, depending generally on the basicity of the catalyst.

The non-tertiary amines from which the hydroxyl-containing tertiary amine adducts are prepared can be straight chain or branch chain and include, by way of illustration, radicals derived from such aliphatic (which term includes cycloaliphatic unless the context indicates otherwise) non-tertiary amines as ethyl amine, n-propyl amine, isopropyl amine, n-butyl amine, isobutyl amine, cyclopropyl amine, cyclobutyl amine, cyclopentyl amine, cyclohexyl amine, n-amyl, isoamyl amine, n-hexyl amine, isohexyl amine, 2-ethyl hexyl amine, 2-ethyl octyl amine, n-nonyl amine, isononyl amine, n-decyl amine, isodecyl amine, undecyl amine, n-dodecyl amine, isododecyl amine, tridecyl amine, tetradecyl amine, pentadecyl amine, hexadecyl amine, heptadecyl amine and octadecyl amine, and mixtures thereof as in commercial mixtures of fatty and other non-tertiary amines. The non-tertiary amines include the secondary amines corresponding to the primary amines mentioned above, as, for example, di-n-propyl amine, di-n-butyl amine, etc.

The α-epoxides which are utilized in the preparation of the novel compounds of the present invention and from which the radical

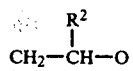

of formula (I) is derived include, by way of illustrative examples, propylene oxide; butylene, pentylene, hexylene, heptylene, octylene, nonylene, decylene, dodecylene, tetradecylene, pentadecylene, hexadecylene and octadecylene oxides, as well as styrene oxide and similar α-epoxides derived from analogous alkenyl benzenes.

Illustrative examples of chemical compounds falling within the scope of our invention are the following:

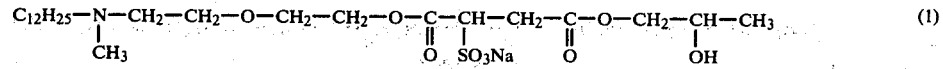

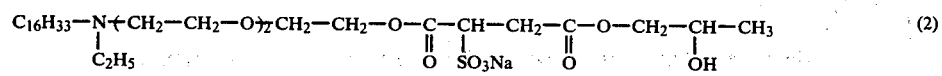

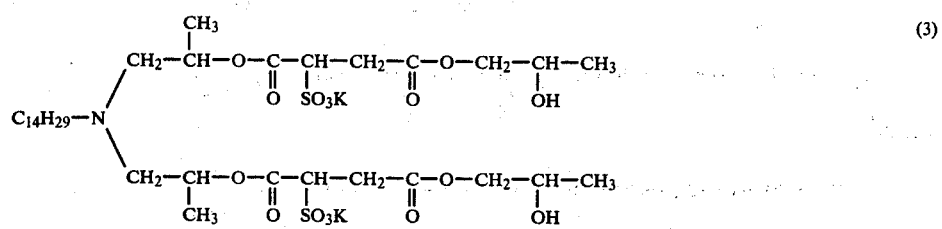

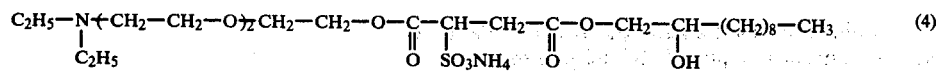

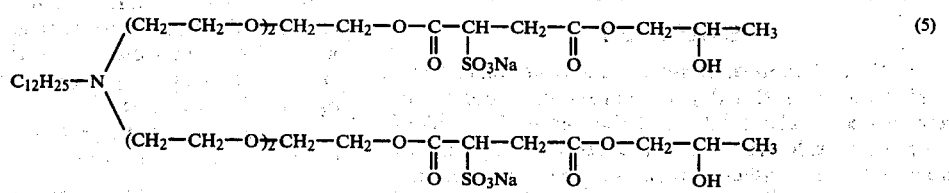

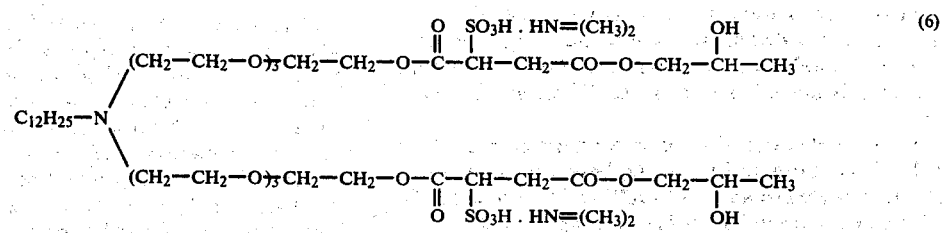

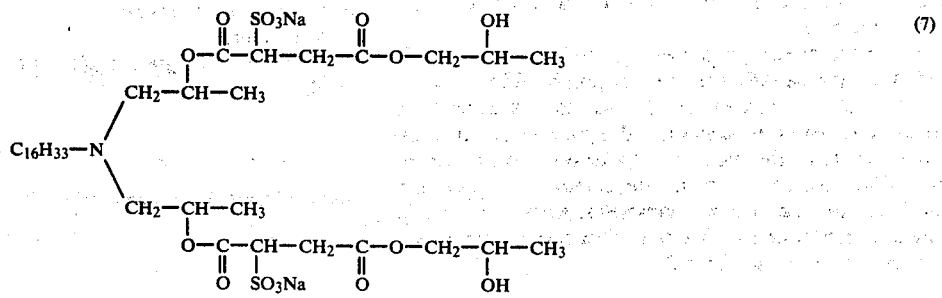

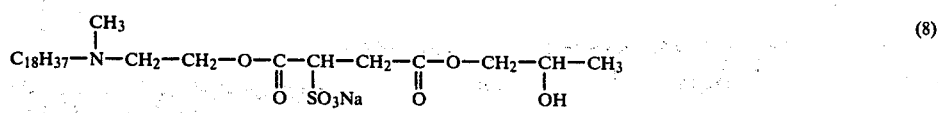

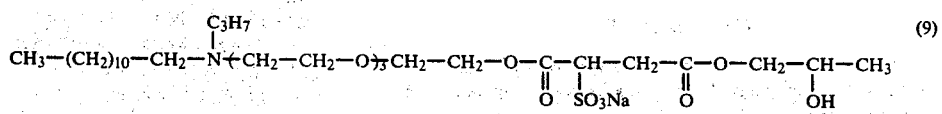

-continued

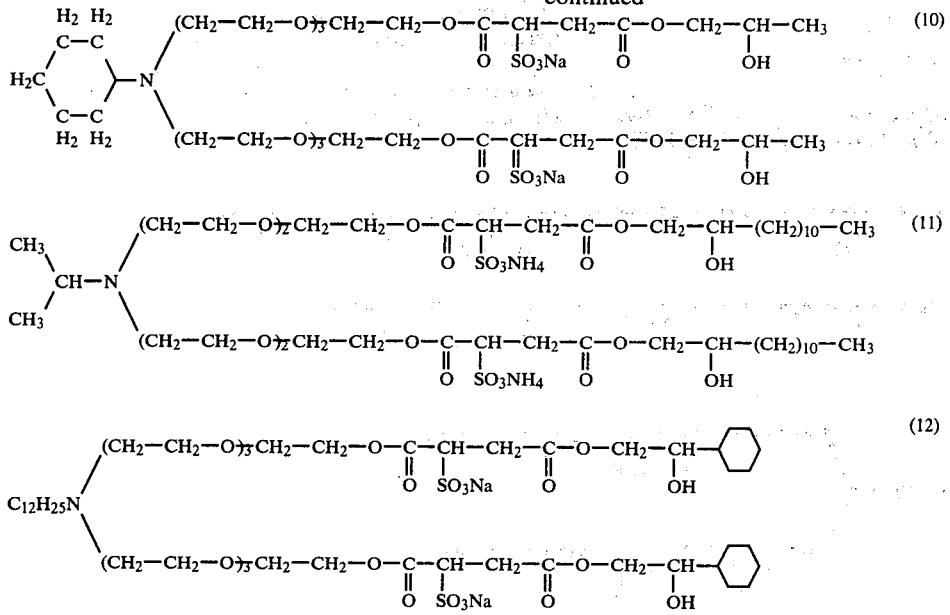

The following examples are illustrative of the preparation of typical compounds of the present invention. All temperatures recited are in degrees Centigrade.

EXAMPLE I (a) 224 g (1 mol) of di-n-octyl amine are placed in a flask provided with a dry ice sparger and a condenser and heated to about 110°, and then 64 g (1.1 mol) of propylene oxide are gradually added over a period of about 4 hours to effect adduction of the amine with the propylene oxide. The reaction mixture is then cooled to about 45° and a total of 103 g (1.05 mols) of maleic anhydride are added in three substantially equal proportions in a period of about 1 hour, and then the resulting reaction mixture is heated at about 90° for an additional hour.

(b) The monoester of the di-n-octyl amine-propylene oxide adduct produced in part (a) hereof is placed in an autoclave heated to about 90°–100° and to it is added 70 g (1.2 mols) of propylene oxide over a period of about 2 hours, at the end of which time the acid value is less than 0.1 meq/g.

(c) To the diester produced in part (b) hereof there is added 273 g of a 40% aqueous sodium bisulfite solution (1.05 mols) and heated to 90°. An almost immediate exothermic reaction occurs and the pressure in the autoclave rises to of the order of 5 to 10 pounds per square inch. The reaction is complete in about ½ hour. On cooling, a generally clear, somewhat amber solution is obtained containing a diester sulfosuccinate surfactant corresponding to the formula:

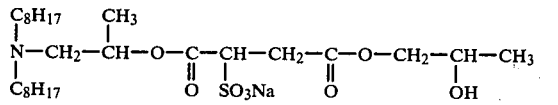

EXAMPLE II

A diester is produced in accordance with parts (a) and (b) of Example I and there is admixed therewith 100 g of isopropanol and 50 g of water and the resulting mixture is placed in an autoclave. There is then added thereto 67 g (1.05 mols) of sulfur dioxide at about 50°, and the resulting mixture is heated to 100°. The reaction occurs almost immediately and the pressure rises in the autoclave to about 15 pounds per square inch. On cooling, the diester sulfosuccinate, in the form of an amine salt due to Zwitterion effect, is present in the form of a generally clear amber solution.

EXAMPLE III

The procedure described in Example I is carried out except that, in part (a), in place of the 244 g of di-n-octyl amine, there is used 287 g (1 mol) of an adduct made from 1 mol of methyl dodecyl amine with 2 mols of ethylene oxide. The balance of Example I is carried out using the same amounts of the specified ingredients. The diester sulfosuccinate product obtained corresponds to the formula of Example (1) of the illustrative examples listed above of chemical compounds falling within the scope of our invention.

We claim:

1. A sulfosuccinate surfactant according to the formula

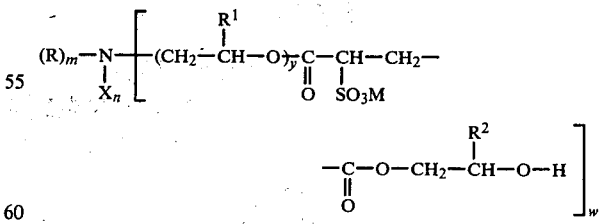

where R is alkyl; X is alkyl; $R^1$ is H or $CH_3$; $R^2$ is an alkyl having from 1 to 18 carbon atoms; M is a cation selected from the group of alkali metal, alkaline earth metal, ammonium, and water soluble organic amines; m is 1 or 2; n is zero or 1; y is 1 to 10 when $R^1$ is H and from 1 to 3 when $R^1$ is $CH_3$; w is 1 or 2; with the proviso that the number of carbon atoms in $(R)_m$ is from 2 to 24, and that there is a difference of at least 2 in the number of carbon atoms between the sum of the carbon atoms in (i)

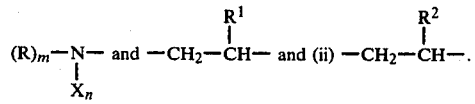

2. A surfactant according to claim 1, in which the difference in the number of carbon atoms between the sum of the carbon atoms in (i) $(R)_m$—$N(X)_n$ and

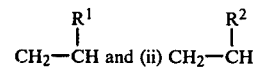

is from 4 to 14.

3. A surfactant according to claim 1, in which R is alkyl containing from 8 to 15 carbon atoms, X is alkyl containing from 1 to 8 carbon atoms, $R^1$ is H, $R^2$ is $CH_3$, y is 2 to 6, and w is 1.

4. A surfactant according to claim 3, in which R is a straight chain alkyl.

5. A surfactant according to claim 1, in which R contains from 3 to 18 carbon atoms and is a branch chain alkyl.

6. A surfactant according to claim 1, in which $(R)_m$ is a $C_2$-$C_5$ alkyl, $R^1$ is H where y is 2 to 6, and $R^2$ is alkyl containing from 1 to 18 carbon atoms.

7. A surfactant according to claim 1 which is represented by the formula:

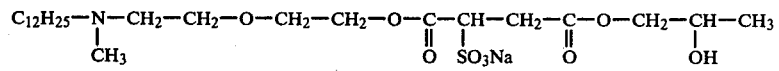

* * * * *